US009149181B2

(12) United States Patent
Matsumoto et al.

(10) Patent No.: US 9,149,181 B2
(45) Date of Patent: Oct. 6, 2015

(54) TOMOGRAPHIC IMAGING APPARATUS AND PHOTOGRAPHING METHOD

(75) Inventors: Kazuhiro Matsumoto, Yokohama (JP); Nobuhito Suehira, Kawasaki (JP); Nobuhiro Tomatsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 85 days.

(21) Appl. No.: 13/282,778

(22) Filed: Oct. 27, 2011

(65) Prior Publication Data
US 2012/0189184 A1    Jul. 26, 2012

(30) Foreign Application Priority Data

Jan. 20, 2011  (JP) .................................. 2011-010150

(51) Int. Cl.
*G06K 9/00* (2006.01)
*A61B 3/10* (2006.01)

(52) U.S. Cl.
CPC ....................................... *A61B 3/102* (2013.01)

(58) Field of Classification Search
USPC ...................... 382/128, 131; 351/206; 396/18
See application file for complete search history.

(56) References Cited

U.S. PATENT DOCUMENTS

| 4,820,037 | A | * | 4/1989 | Kohayakawa et al. ........ 351/211 |
| 4,848,896 | A | * | 7/1989 | Matsumoto |
| 4,952,049 | A | * | 8/1990 | Matsumoto |
| 5,321,501 | A | * | 6/1994 | Swanson et al. .............. 356/479 |
| 5,615,278 | A | * | 3/1997 | Matsumoto |
| 6,137,585 | A | * | 10/2000 | Hitzenberger et al. ....... 356/484 |
| 6,288,784 | B1 | * | 9/2001 | Hitzenberger et al. ....... 356/485 |
| 6,293,674 | B1 | * | 9/2001 | Huang et al. .................. 351/221 |
| 6,296,358 | B1 | * | 10/2001 | Cornsweet et al. ........... 351/206 |
| 6,307,634 | B2 | * | 10/2001 | Hitzenberger et al. ....... 356/484 |
| 6,779,890 | B2 | * | 8/2004 | Matsumoto |
| 7,136,518 | B2 | * | 11/2006 | Griffin et al. |
| 7,198,777 | B2 | * | 4/2007 | Boppart et al. |
| 7,348,563 | B2 | * | 3/2008 | Fujita ........................ 250/363.04 |
| 7,365,858 | B2 | * | 4/2008 | Fang-Yen et al. ............. 356/489 |
| 7,446,882 | B2 | * | 11/2008 | De Lega et al. ............... 356/512 |
| 7,458,684 | B2 | * | 12/2008 | Fukuma et al. ............... 351/205 |
| 7,458,686 | B2 | * | 12/2008 | Ikezawa ........................ 351/222 |
| 7,549,746 | B2 | * | 6/2009 | Tsukada et al. ............... 351/206 |

(Continued)

FOREIGN PATENT DOCUMENTS

| JP | 2002-515593 A | 5/2002 |
| JP | 2006-122649 A | 5/2006 |

(Continued)

*Primary Examiner* — Chan Park
*Assistant Examiner* — Iman K Kholdebarin
(74) *Attorney, Agent, or Firm* — Fitzpatrick, Cella, Harper & Scinto

(57) ABSTRACT

A tomographic imaging apparatus includes: a light source; an optical splitter unit for splitting light from the light source into reference light and measuring light; a reference optical system including an adjustment unit for adjusting an optical path length of the reference light; a spectral unit for spectrally splitting combined light of the reference light and the return light obtained by irradiating an object to be inspected with the measuring light so as to acquire an interfering signal; a detection unit for detecting an optical path length when a tomographic image of the object is photographed; a storage unit for recording data about a refractive index of a refracting element of the object; and a calculation unit for calculating image data from the interfering signal acquired by the spectral unit based on an actual size using data about the optical path length and the refractive index.

13 Claims, 6 Drawing Sheets

(56) References Cited

U.S. PATENT DOCUMENTS

| | | | |
|---|---|---|---|
| 7,566,128 B2 * | 7/2009 | Tsukada et al. | 351/205 |
| 7,583,385 B2 | 9/2009 | Kato | |
| 7,756,311 B2 * | 7/2010 | Yasuno et al. | 382/128 |
| 7,905,597 B2 * | 3/2011 | Tsukada et al. | 351/206 |
| 7,980,697 B2 * | 7/2011 | Tsukada et al. | 351/208 |
| 8,098,278 B2 * | 1/2012 | Yumikake et al. | 348/78 |
| 8,125,645 B2 * | 2/2012 | Ozawa | 356/477 |
| 8,204,300 B2 * | 6/2012 | Sugita et al. | 382/154 |
| 8,205,988 B2 * | 6/2012 | Fujii et al. | 351/205 |
| 8,379,218 B2 * | 2/2013 | Deck et al. | 356/479 |
| 8,384,908 B2 | 2/2013 | Sugita et al. | |
| 8,517,537 B2 * | 8/2013 | Suehira et al. | 351/208 |
| 8,801,180 B2 | 8/2014 | Hayashi et al. | |
| 2001/0000978 A1 * | 5/2001 | Hitzenberger et al. | |
| 2003/0199769 A1 * | 10/2003 | Podoleanu et al. | 600/476 |
| 2005/0105097 A1 * | 5/2005 | Fang-Yen et al. | 356/497 |
| 2006/0077395 A1 * | 4/2006 | Chan et al. | 356/497 |
| 2006/0087616 A1 * | 4/2006 | Hanebuchi | |
| 2006/0121123 A9 * | 6/2006 | Boppart et al. | |
| 2006/0187462 A1 * | 8/2006 | Srinivasan et al. | 356/479 |
| 2007/0002276 A1 * | 1/2007 | Hirohara et al. | 351/206 |
| 2007/0076213 A1 * | 4/2007 | Kato | |
| 2007/0076217 A1 * | 4/2007 | Baker et al. | 356/498 |
| 2007/0086011 A1 * | 4/2007 | Toida | 356/450 |
| 2007/0159596 A1 * | 7/2007 | Fukuma et al. | |
| 2007/0165210 A1 * | 7/2007 | Wang et al. | |
| 2007/0236660 A1 * | 10/2007 | Fukuma et al. | |
| 2007/0236699 A1 * | 10/2007 | Chou et al. | 356/489 |
| 2008/0025459 A1 * | 1/2008 | Shi et al. | 378/10 |
| 2008/0084538 A1 * | 4/2008 | Maeda et al. | 351/206 |
| 2008/0208525 A1 * | 8/2008 | Kikawa et al. | 702/172 |
| 2008/0316425 A1 * | 12/2008 | Blum et al. | 351/169 |
| 2009/0168017 A1 * | 7/2009 | O'Hara et al. | 351/205 |
| 2009/0190092 A1 * | 7/2009 | Tsukada et al. | 351/208 |
| 2009/0244547 A1 | 10/2009 | Ozawa | |
| 2009/0270738 A1 * | 10/2009 | Izatt et al. | 600/476 |
| 2010/0014089 A1 * | 1/2010 | Yamada et al. | 356/450 |
| 2010/0118132 A1 * | 5/2010 | Yumikake et al. | 348/78 |
| 2010/0142780 A1 * | 6/2010 | Yasuno et al. | 382/131 |
| 2010/0166293 A1 * | 7/2010 | Sugita et al. | 382/154 |
| 2010/0189334 A1 * | 7/2010 | Tomidokoro et al. | 382/131 |
| 2010/0194757 A1 * | 8/2010 | Tomidokoro et al. | 345/440 |
| 2010/0321700 A1 * | 12/2010 | Hirose et al. | 356/450 |
| 2010/0328608 A1 * | 12/2010 | Fujii et al. | 351/211 |
| 2011/0051088 A1 * | 3/2011 | Shimizu et al. | 351/206 |
| 2011/0058175 A1 * | 3/2011 | Suehira | 356/450 |
| 2011/0080561 A1 * | 4/2011 | Hayashi et al. | 351/206 |
| 2011/0243408 A1 * | 10/2011 | Takama | 382/128 |
| 2011/0299035 A1 * | 12/2011 | Suehira | 351/206 |
| 2012/0013915 A1 * | 1/2012 | Okamura et al. | 356/479 |
| 2012/0044499 A1 | 2/2012 | Shimoyama et al. | |
| 2012/0083667 A1 * | 4/2012 | Isogai et al. | 600/300 |
| 2012/0092615 A1 * | 4/2012 | Izatt et al. | 351/206 |
| 2012/0133950 A1 | 5/2012 | Suehira et al. | |
| 2012/0188510 A1 | 7/2012 | Suehira et al. | |
| 2012/0189184 A1 * | 7/2012 | Matsumoto et al. | 382/131 |
| 2012/0218557 A1 * | 8/2012 | Sugita et al. | 356/479 |
| 2012/0229764 A1 * | 9/2012 | Tomatsu et al. | 351/206 |
| 2013/0003075 A1 * | 1/2013 | Kusumoto | 356/479 |
| 2013/0003077 A1 * | 1/2013 | Suehira et al. | 356/479 |

FOREIGN PATENT DOCUMENTS

| | | | |
|---|---|---|---|
| JP | 2007-101268 A | | 4/2007 |
| JP | 2007117714 A | * | 5/2007 |
| JP | 2008154704 A | * | 7/2008 |
| JP | 2008-298767 A | | 12/2008 |
| JP | 2009-244232 A | | 10/2009 |
| JP | 2010-000191 A | | 1/2010 |

* cited by examiner

|  | CURVATURE RADIUS | | THICKNESS | REFRACTIVE INDEX |
|---|---|---|---|---|
| CORNEA | FRONT SURFACE | 7.8 | 0.5 | 1.38 |
|  | REAR SURFACE | 6.5 | | |
| ANTERIOR CHAMBER |  |  | 3.0 | 1.34 |
| CRYSTALLINE LENS | FRONT SURFACE | 10.0 | 4.0 | 1.42 |
|  | REAR SURFACE | -6.0 | | |
| CORPUS VITREUM |  |  |  | 1.34 |

TOMOGRAPHIC IMAGING APPARATUS AND PHOTOGRAPHING METHOD

BACKGROUND OF THE INVENTION

1. Field of the Invention

The present invention relates to a tomographic imaging apparatus, and more particularly, to a tomographic imaging apparatus and a photographing method that use optical coherence tomography that is used for observation of a fundus and the like.

2. Description of the Related Art

A photographing apparatus using optical coherence tomography (OCT) in which interference due to low coherent light is utilized (hereinafter, also referred to as OCT apparatus) is now put into practical use. The photographing apparatus is capable of acquiring a tomographic image at a resolution that substantially corresponds to the wavelength of light entering an object to be inspected, which thus leads to high-resolution photographing of a tomographic image of the object.

In an OCT apparatus, light from a light source is split into measuring light and reference light by a beam splitter or the like. The measuring light irradiates an object to be inspected, such as an eye, via a measuring light path. Then, return light from the object to be inspected is combined with reference light and is guided to a detector as interfering light via a detection optical path. Here, the return light refers to reflected light and scattered light including information about an interface in the light-irradiation direction with respect to the object to be inspected. The interfering light of the return light and the reference light is detected by the detector and is analyzed so that a tomographic image of the object to be inspected can be obtained.

The OCT apparatus is used for photographing a tomographic image of a fundus retina in many cases, but there is also known a method of photographing the fundus widely so as to determine an eyeball shape (see Japanese Patent Application Laid-Open No. 2006-122649).

However, the eyeball shape determined in this way is calculated from a tomographic image formed based on a principle of the OCT, and therefore indicates an optical distance including information on a refractive index but does not indicate an actual shape and an actual size.

SUMMARY OF THE INVENTION

A tomographic imaging apparatus according to the present invention, which is capable of displaying an actual shape and an actual size of the above-mentioned tomographic image of a retina or the like, is an image photographing apparatus for acquiring a tomographic image of an object to be inspected based on combined light of return light from the object to be inspected and reference light, the return light being obtained by irradiating the object to be inspected with measuring light, the reference light corresponding to the measuring light. The apparatus includes: a storage unit for storing data about optical information of the object to be inspected; and a calculation unit for calculating data about a second tomographic image based on an optical path length of the reference light and data about optical information of the object to be inspected, which correspond to a first tomographic image of the object to be inspected, and a signal of the combined light corresponding to the first tomographic image.

According to the present invention, it is possible to obtain tomographic image data close to an actual size and an actual shape of the object to be inspected.

Further features of the present invention will become apparent from the following description of exemplary embodiments with reference to the attached drawings.

DESCRIPTION OF THE EMBODIMENTS

First Embodiment

Hereinafter, an embodiment of the present invention is described in detail with reference to the attached drawings. An apparatus of this embodiment can photograph tomographic images of a retina, an anterior ocular, and the like of a human eye, for example.

In addition, the eye to be inspected in the following embodiment corresponds to an object to be inspected, the retina corresponds to a region to be inspected, and an eyeball axis corresponds to an optical axis of the object to be inspected, in the present invention.

(Structure of Apparatus)

Figure 1:
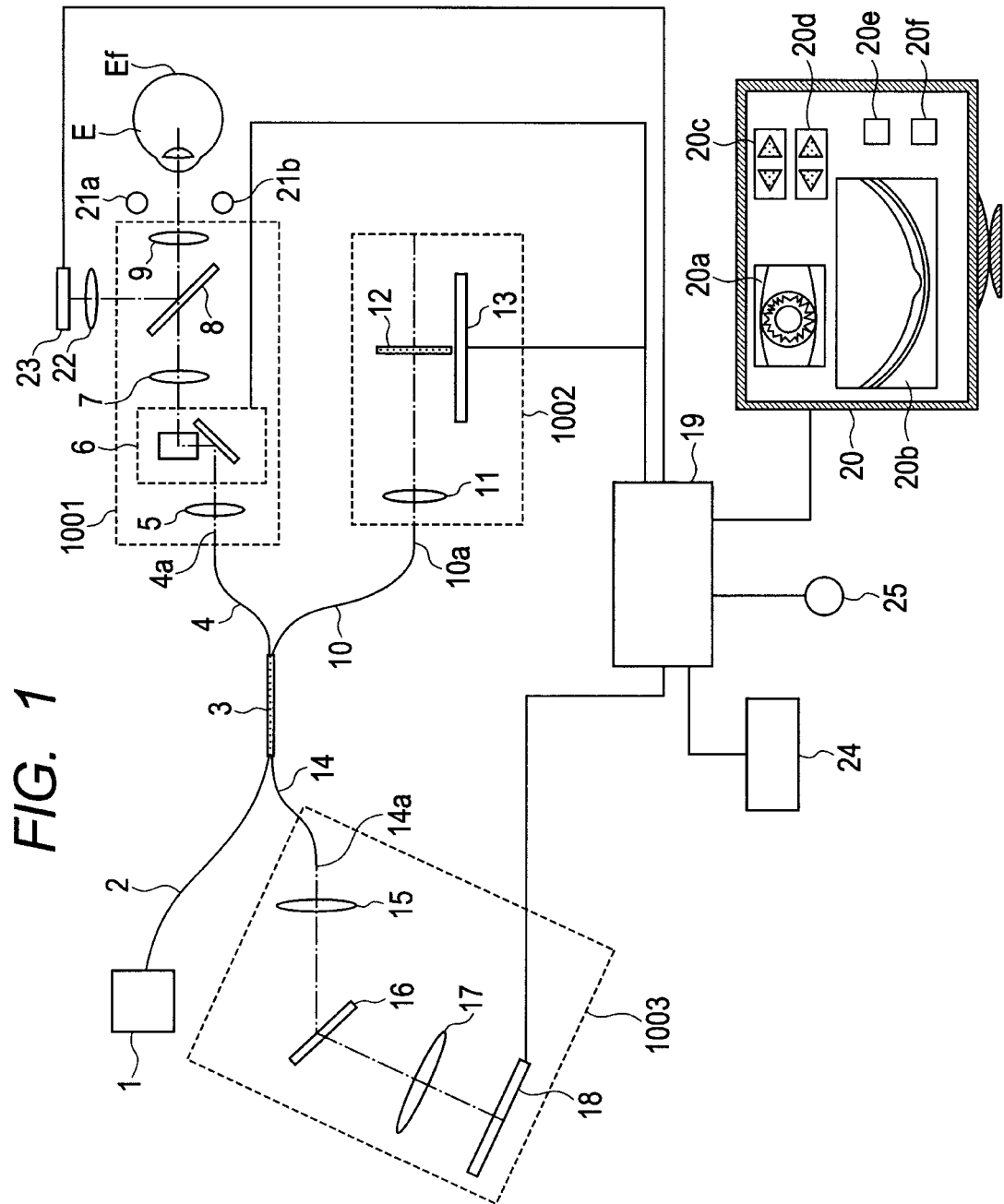
FIG. 1 is a schematic diagram illustrating an outline of an OCT apparatus according to a first embodiment of the present invention.

An example in which Fourier domain optical coherence tomography according to this embodiment is applied to a fundus photographing or imaging apparatus is described with reference to FIG. 1.

The fundus photographing apparatus includes a light source 1 for generating light (low coherence light), which corresponds to a light source unit of the present invention. In this embodiment, a super luminescent diode (SLD) light source having a center wavelength of 850 nm and a bandwidth of 50 nm is used as the light source 1. Note that an amplified spontaneous emission (ASE) light source may be used as the light source 1. In addition, an ultrashort pulse laser light source, such as a titanium sapphire laser, may be used as the light source 1. In this way, any light source that can generate low coherence light may be used as the light source 1. Further, a wavelength of light generated from the light source 1 is not limited particularly and is selected in the range from 400 nm to 2 μm according to the object to be inspected. As the band width of the wavelength increases, the vertical resolution increases. In general, in the case where the center wavelength is 850 nm, a bandwidth of 50 nm makes a vertical resolution of 6 μm while a bandwidth of 100 nm makes a vertical resolution of 3 μm.

The fundus photographing apparatus includes light guide portions 2, 4, 10, and 14 constituted of an optical fiber or the like. A light beam emitted from the light source 1 is guided by the light guide portion 2 to an optical splitter 3. The optical splitter 3 may be constituted of a fiber coupler or the like and corresponds to an optical splitter unit of the present invention. Note that a split ratio is set to an appropriate value in accordance with the object to be inspected.

On the optical path of the light split by the optical splitter 3 to the light guide portion 4 side, there are disposed a collimator lens 5, an optical scan portion 6, a focus lens 7, a wavelength split mirror 8, and an objective lens 9, which constitute a sample arm 1001. The optical scan portion 6 is constituted of Galvano mirrors, resonance mirrors, or the like, which are disposed to be close to each other in the optical-axis direction (in a tandem arrangement) so as to scan the light beam in x and y directions that are orthogonal to each other. The wavelength split mirror 8 transmits the light from the light source 1 (having a wavelength λ of 800 to 900 nm) and reflects the light for illuminating the anterior ocular (λ=940 nm). The light guided to the light guide portion 4 propagates as measuring light in the sample arm 1001 to reach a fundus Ef of an eye E to be inspected.

On the optical path of the light split by the optical splitter 3 to the light guide portion 10 side, there are disposed a collimator lens 11 and a reference mirror 12, which constitute a reference arm 1002. The reference mirror 12 is disposed on a linear positioning stage 13, and an optical path length of the reference arm 1002 is adjusted by moving the linear positioning stage 13 in the optical-axis direction. The reference mirror 12 and the linear positioning stage 13 correspond to an adjustment unit that adjusts the optical path length of the reference light in the present invention, together with a control portion 19 described later.

A lens 15, a spectral portion 16 constituted of a grating as a diffraction grating, a prism, or the like, an imaging lens 17, and an imaging portion 18 including a photoelectric transducer, such as a CMOS sensor or a CCD, constitute a spectroscope 1003. The light guide portion 14 connected to the optical splitter 3 guides the light from the optical splitter 3 to the spectroscope 1003. The control portion 19 controls the optical scan portion 6, the linear positioning stage 13, the imaging portion 18, and the like. In addition, the control portion 19 is connected to a display portion 20.

Anterior ocular illumination light sources 21a and 21b are disposed around the objective lens 9, and an image of the anterior ocular of the eye E to be inspected that is illuminated by these light sources passes through the objective lens 9 and is reflected by the wavelength split mirror 8 to be formed on an imaging plane of a two-dimensional imaging portion 23 by a lens 22. In addition, the control portion 19 is connected to a memory 24 and a pointing device 25 such as a mouse.

(Measuring Method)

Next, a method of photographing or imaging a tomographic image of the retina of the fundus Ef of the eye E to be inspected using the apparatus having the above-mentioned structure, namely a tomographic image photographing method is described.

When the eye E to be inspected is set in front of this apparatus, the anterior ocular of the eye E to be inspected is illuminated by light emitted from the light sources 21a and 21b. An image of the anterior ocular illuminated in this manner passes through the objective lens 9 and is reflected by the wavelength split mirror 8 to be formed on the imaging plane of the imaging portion 23 by the lens 22. An image signal from the imaging portion 23 is input to the control portion 19 and is converted into digital data in real time so that an anterior ocular image is generated. The control portion 19 determines the eccentricity of the eye E to be inspected and a focus state based on the anterior ocular image, particularly a pattern of an iris of the eye E to be inspected. Because the center of the imaging plane is adjusted to coincide with the optical axis of the optical system of the sample arm 1001, an eccentricity amount between the imaging center and the pupil center of the anterior ocular image photographed by the imaging portion 23 corresponds to an eccentricity amount between the eye E to be inspected and the optical system of the sample arm 1001. The optical system of the sample arm 1001 is disposed on a stage (not shown) in a manner capable of adjusting its position with respect to the eye E to be inspected in the vertical and horizontal directions and in the optical-axis direction. Therefore, as described above, the positions in the vertical and horizontal directions are adjusted so that the pupil center coincides with the optical axis. Further, the position in the optical-axis direction is adjusted so that contrast of the iris pattern becomes highest. Thus, a distance (working distance) between the objective lens 9 of the optical system of the sample arm 1001 and the pupil Ep of the eye E to be inspected that is on the same plane as the iris is maintained to be constant. The anterior ocular image is displayed on a display region 20a of the display portion 20, and the operator can confirm the optical axis eccentricity based on this image.

In this way, when the eccentricity amount becomes a predetermined value or smaller by automatic alignment, the light source 1 is turned on so as to start photographing of a tomographic image for alignment. The light from the light source 1 is guided to the optical splitter 3 by the light guide portion 2 and is split so that the ratio of light intensity between light guided to the light guide portion 4 and light guided to the light guide portion 10 becomes 1:9, for example. The measuring light guided to the light guide portion 4 side reaches a fiber end 4a. The measuring light exiting from the fiber end 4a as a point light source is collimated by the collimator lens 5 and is deflected by an X scan mirror of the scan portion 6. The collimated measuring light passes through the focus lens 7 and the wavelength split mirror 8, and irradiates the fundus Ef through the objective lens 9 and the pupil of the eye E to be inspected so as to scan the fundus Ef.

Return light reflected and scattered by multiple layers constituting the retina of the fundus Ef comes back along the same optical path as incident light, enters the light guide portion 4 via the collimator lens 5 and the fiber end 4a, and is guided to the optical splitter 3. The return light exiting from a fiber end 14a via the light guide portion 14 is collimated by the collimator lens 15 and enters the spectral portion 16. A large number of diffraction gratings having a similar size to a wavelength of the measuring light are formed at a constant interval in the spectral portion 16, and spectrally split the incident return light by diffraction.

Because the diffraction angle is different depending on the wavelength, the diffracted return light forms a line image by the imaging lens 17 in the linear imaging region of the imaging portion 18. In other words, the return light exiting from the fiber end 14a forms a spectral slit image. Therefore, the imaging portion 18 outputs a signal corresponding to the intensity of each wavelength. The structure of the optical splitter 3 and the like for combining the return light and the reference light to generate the combined light, the structure of the spectral portion 16 and the like for spectrally splitting the combined light, and the structure of the imaging portion 18 and the like for generating the interfering signal from the combined light correspond to the spectral unit of the present invention.

In addition, the reference light guided by the optical splitter 3 to the light guide portion 10 exits from a fiber end 10a and is collimated by the lens 11 so as to be directed to the reference mirror 12. The reference mirror 12 is disposed on the linear positioning stage 13 in a movable manner in the direction perpendicular to the optical axis of the reference light as collimated light, and further, in the optical-axis direction. Thus, the optical path length of the reference light can coincide with the optical path length of the measuring light for eyes E to be inspected having different axial lengths. The operator can adjust the position of the reference mirror 12 by operating the pointing device 25 to designate a display region 20d on the display portion 20 with a cursor. The reference light reflected by the reference mirror 12 is condensed by the lens 11 to the fiber end 10a of the light guide portion 10, and is guided to the light guide portion 14 by the light guide portion 10 via the optical splitter 3. Then, the light guided to the light guide portion 14 is combined with the return light from the fundus E, and the combined light enters the spectroscope 1003. Then, as described above, the light is spectrally split by the spectral portion 16 and forms an image on a light receiving region of the imaging portion 18 on which photoelectric transducers are arranged linearly. A signal from the imaging portion 18 is input to the control portion 19 in which a tomographic image is generated to be displayed on a display region 20b of the display portion 20. The operator observes this tomographic image and operates a button in a display region 20c with a cursor using the pointing device 25 for focus adjustment so that the tomographic image becomes brightest. In addition, similarly, the operator operates a button in the display region 20d for position adjustment of the reference mirror 12 (coherence gate adjustment) so that the tomographic image of the concerned part is all in a desired region of the display region 20b. When the display region 20d is designated, the control portion 19 moves the position of the linear positioning stage 13 in the designated direction and changes control position information of the linear positioning stage 13 stored in the memory 24 according to a movement amount. The linear positioning stage 13 is driven and controlled by a stepping motor (not shown), and a position of the linear positioning stage 13 corresponds to the number of steps to be instructed to the stepping motor. For instance, when a stroke of 60 mm is driven by 60,000 steps, a movement amount per step is 1 μm. The number of steps from 0 to 60,000 corresponds to the position of the linear positioning stage from 0 to 60 mm. In addition, the distance between a reference position of the linear positioning stage 13 and the lens 11 is arranged accurately in design, and the relationship between this reference position and the stage position is also clear in design. Therefore, the optical path length of the reference light can be calculated based on the number of steps. The control portion 19 corresponds to a detection unit in the present invention that detects the optical path length based on the number of steps of the stepping motor (not shown). In this way, the optical path length of the reference light varies along with a positional variation of the reference mirror 12. Thus, a display position of the tomographic image in the display region 20b is changed. In this way, a position of the reference mirror 12 in photographing a tomographic image is always stored in the memory 24. After preparation for photographing as described above, when a photograph button 20e is operated, still image photographing of a tomographic image (tomographic image photographing) is performed. Thus, a photographed tomographic image is stored in the memory 24.

(Tomographic Image Generation)

Next, tomographic image generation is described.

The combined light of the return light from the fundus Ef of the eye E to be inspected and the reference light reflected by the reference mirror 12 is guided to the light guide portion 14. Because of a difference between the optical path length from the optical splitter 3 to the fundus Ef and the optical path length from the optical splitter 3 to the reference mirror 12, there is a phase difference between the return light and the reference light when being combined by the optical splitter 3. Because this phase difference is different depending on the wavelength, the spectral intensity distribution that appears on a light receiving region 18a of the imaging portion 18 has an interference pattern. In addition, the retina has multiple layers, and the return light rays from individual layer boundaries have different optical path lengths. Therefore, the interference patterns include interference patterns having different frequencies. Based on the frequencies and intensities of the interference patterns included in the intensity distribution, a position of a reflecting object and the luminance corresponding to reflection and scattering from the position can be determined.

In a B-scan mode for scanning one line on the fundus, the control portion 19 drives only one of the X scan mirror and the Y scan mirror, for example, only the X scan mirror of the optical scan portion 6, while reading the output from the imaging portion 18. The scan portion 6 outputs data indicating an angle of the scan mirror, and the read signal is converted into digital data together with a scan-mirror angle, and is further converted into an incident angle θi of the light into the eye to be inspected, which is then stored in the memory 24.

The scan-mirror angle corresponds to the incident angle θi of the light ray and is determined from a design value of the optical system. Note that, the incident angle θi corresponds to a first angle between the measuring light entering the eye to be inspected and the eyeball axis of the eye to be inspected.

Figure 2:
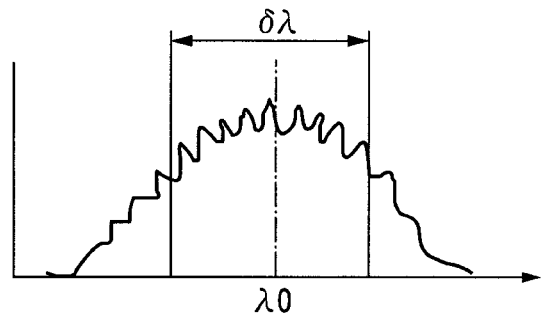
FIG. 2 is a diagram illustrating a shape of a signal according to the first embodiment of the present invention.

FIG. 2 illustrates the optical intensity distribution on the imaging portion 18 at the scan-mirror angle θi. The horizontal axis represents a sensor position on the imaging portion 18 and corresponds to the wavelength. The vertical axis represents signal intensity. Here, with respect to intensity distribution of the center wavelength of λ0 and a half-width δλ, waveforms due to the interference pattern are superimposed.

Figure 3:
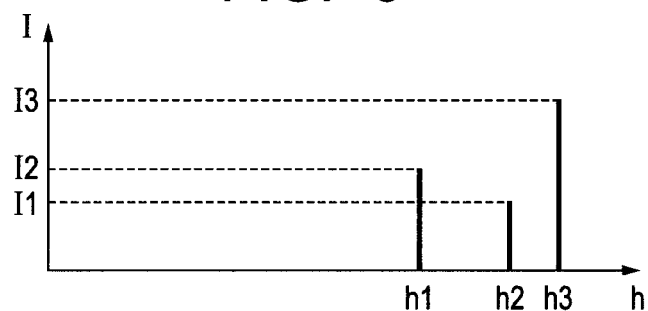
FIG. 3 is a diagram illustrating an output signal according to the first embodiment of the present invention.
Figure 4:
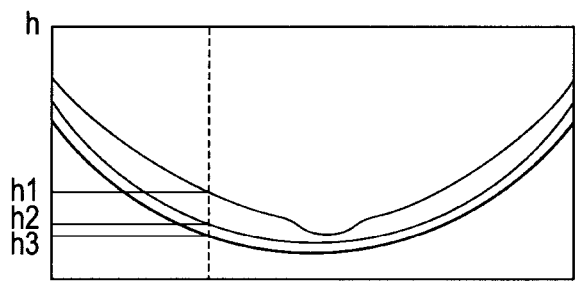
FIG. 4 is a diagram illustrating a tomographic image of the first embodiment of the present invention.

This waveform intensity information is read out and is converted by an A/D converter into digital data, which is stored in the memory 24. Wave number conversion and frequency conversion of the data are performed, and hence the intensity distribution as illustrated in FIG. 3 is obtained. This indicates that interference intensities at distances (from the coherence gate) h1, h2, and h3 are I2, I1, and I3 as illustrated in FIG. 4. Therefore, the interference intensity is measured while the scan-mirror angle θi is changed from θs to θe. The interference intensity I(θi, hj) acquired in this way is displayed with θ in the horizontal axis and h in the vertical axis, and hence a B-scan image of the fundus (based on the optical distance) can be displayed as illustrated in FIG. 4.

(Shape Measurement)

Figure 5:
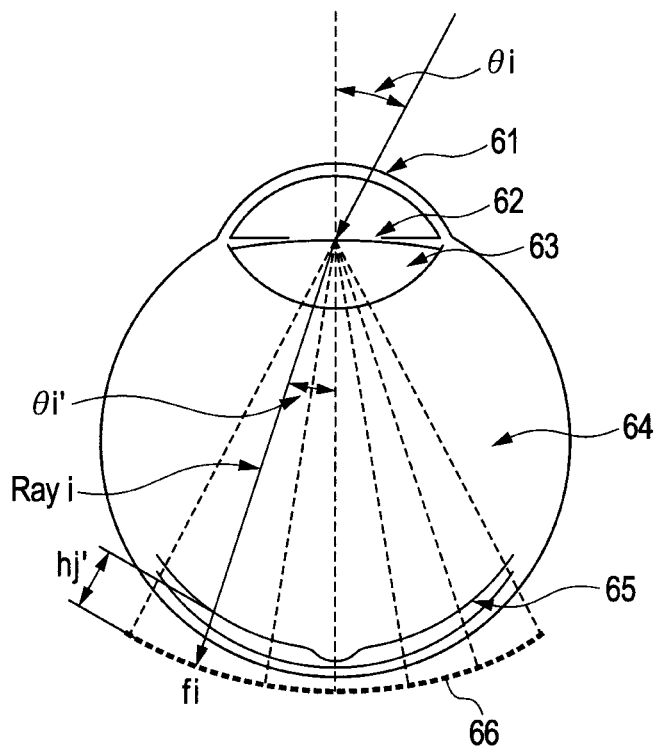
FIG. 5 is a diagram illustrating light rays according to the first embodiment of the present invention

FIG. 5 illustrates the light ray (measuring light) reaching the fundus when the B-scan of the fundus is performed. The light ray entering the eye E to be inspected through a cornea 61 at the incident angle θi passes through a crystalline lens 63 and a corpus vitreum 64 in the middle part of a pupil 62 of the eye E to be inspected, and is directed to a fundus 65 to be reflected and scattered by individual layers of the retina. If a distance between the eye E to be inspected and the optical system of the sample arm 1001 is maintained appropriately by the automatic alignment function, the light ray always passes through the middle portion of the pupil 62 even if the scan angle of the X scan mirror changes, because the X scan mirror is designed to be conjugated with the pupil 62. This point is referred to as a pivot point. The pivot point corresponds to the position through which the measuring light always passes when the measuring light enters the eye E to be inspected and even if the measuring light scans the retina. In other words, the pivot point corresponds to an incident point of the measuring light in the eye E to be inspected when the measuring light scans the retina in the eye E to be inspected in the present invention. A position 66 indicates a position of the same distance as an optical path length of a reference optical system, namely a position equivalent to a reference mirror position (coherence gate). In other words, the distances h1, h2, and h3 determined from the interfering signal respectively correspond to distances between the reference mirror position 66 and the individual retina layers.

When eyes to be inspected having different axial lengths are photographed, the stage 13 is adjusted so that the position of the reference mirror 12 is adjusted to coincide with the axial length. Thus, the measurement can be performed.

Here, the fundus shape obtained from the tomographic image illustrated in FIG. 4 is different from an actual eyeball shape in the following points.

(1) The distance hj determined by the calculation is an optical distance for light to propagate in vacuum in the same time (optical path length=distance×refractive index), which is different from an actual distance.

(2) Data corresponding to the scan-mirror angles are arranged in parallel to generate the image in FIG. 4, but actually, those image data are image data to be expressed on polar coordinates with the scan center (pivot point) as its center.

(3) The angle θi is an incident angle of the light ray and is different from a scan angle in the eye.

In other words, by correcting the above-mentioned points, an eyeball shape closer to the actual size can be determined.

(Correction of Optical Path Length)

Figure 9:
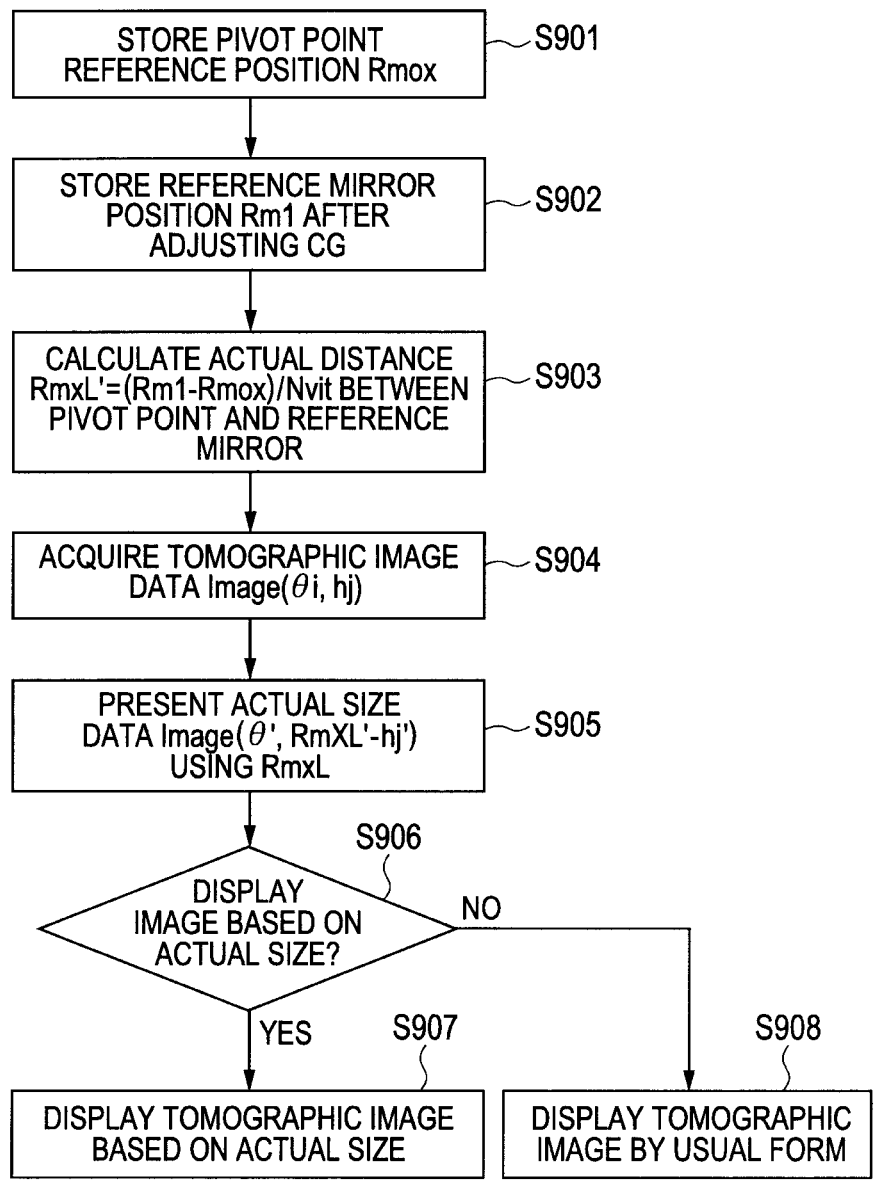
FIG. 9 is a flowchart illustrating a calculation flow according to the first embodiment of the present invention.

The luminance of a point on the B-scan image can be expressed by Image (θi, hj) using parameters of the scan-mirror angle θi and the distance hj that is a difference from the optical path length of the reference optical system, as illustrated in FIG. 4. However, an actual shape cannot be obtained only from this information. The distance hj is a distance from the coherence gate 66, and it is necessary to determine a shape (curvature radius) of this coherence gate surface (CG surface) in order to determine the actual shape. With reference to FIG. 9, a process of determining the actual shape is described.

(Curvature Radius of CG Surface)

This curvature radius is determined from a distance between the pivot point and the coherence gate 66. This distance can be obtained by determining the number of steps corresponding to the position of the reference mirror 12 corresponding to the pivot point based on the design value, and by determining a difference from the number of steps indicating a position of the reference mirror 12 when actual photographing is performed. In addition, the curvature radius can also be measured actually by the following method. The mirror is disposed at the pivot point in front of the objective lens to be perpendicular to the optical axis so that the reflection light comes back to the optical system directly. This light interferes with the return light from the reference mirror 12. Using the operating switch 20d, the stage 13 is driven to move the reference mirror 12, so as to determine a position where a frequency of the interfering signal becomes a minimum, namely a position Rmox having the same optical path length. The number of steps indicating the stage position in this case is stored as an origin of the reference mirror in the memory 24 (Step S901).

Next, the tomographic image data of the eye E to be inspected is acquired. The position of the reference mirror 12 is adjusted so that the shape of the eye E to be inspected is displayed in the screen. In this case, there are two photographing methods. In one method (for photographing an erect image), the optical path length of the reference light is set shorter than the optical path length of the measuring light. In the other method (for photographing a reverse image), the optical path length of the reference light is set longer than the optical path length of the measuring light. Here, the method for photographing a reverse image is described. Using an alignment screen for forming a tomographic image in real time, a position of the stage 13 on which the reference mirror 12 is placed is adjusted so that the tomographic image of the retina of the eye to be inspected is positioned in a vicinity of the CG surface. As described above, the number of steps indicating a position of the stage is regarded as a position Rm1 of the reference mirror (Step S902). In other words, (Rm1−Rmox)×α=RmxL is a distance from the pivot point to the coherence gate 66 (α is a distance corresponding to one step). However, the distance determined from RmxL is an optical distance and is different from an actual distance in the eye to be inspected. The step of determining the above-mentioned distance from RmxL corresponds to the step of acquiring the first position on the optical path of the measuring light, which is an optical path length corresponding to the optical path length of the reference light when a tomographic image is acquired in the optical tomographic image photographing method of the present invention. This step is performed in the control portion 19 by a module region having a function as a first position acquiring unit. Note that, this first position is constituted of a value determined optically. The refractive index Nvit of the corpus vitreum 64 is measured to be substantially the same as that of water (approximately 1.34), and hence the propagation speed of light is slower than that in the air along the reference light path. A ratio of the propagation speed of light is proportional to the reciprocal of the refractive index. Therefore, when a propagation distance of light in the corpus vitreum in a time during which the light propagates by the distance RmxL in the air is denoted by RmxL', RmxL'=RmxL/Nvit=(Rm1−Rmox)/Nvit is satisfied (Step S903). Therefore, the radius of the coherence gate 66 is RmxL'. In this way, by detecting the position of the reference mirror 12, a shape of the surface equivalent to the reference mirror 12 (coherence gate surface) can be known. Therefore, a retina shape in actual size can be determined. Next, the operator operates the photograph button 20e on the display portion. Thus, the control portion 19 calculates the tomographic image based on the signal from the imaging portion 18 as described above and stores the tomographic image data Image(θi, hj) in the memory 24 (Step S904). In the same manner, the actual distance hj' between the surface corresponding to the coherence gate and the retina layer is expressed by hj'=hj/Nvit using the distance hj determined by the measurement and the refractive index Nvit of the corpus vitreum.

(Scan Angle)

Figure 6:
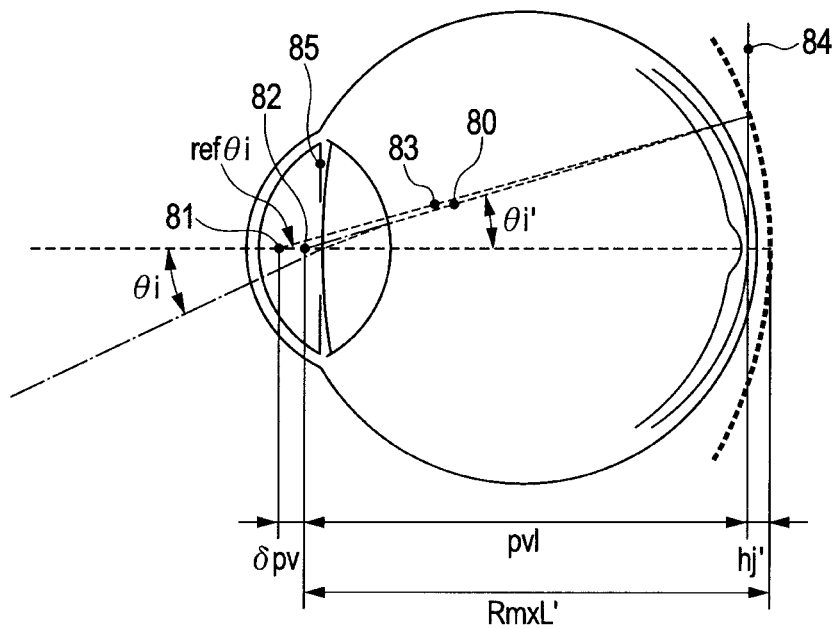
FIG. 6 is a diagram illustrating light rays according to the first embodiment of the present invention.

Next, a method of calculating an angle θ' of an actual scan of an eyeball is described. The incident angle θi of light entering the eye E to be inspected is determined by the scan angle of the scan mirror. An actual scan angle θi' in the eye can be determined based on the axial length of the eye to be inspected, determined with reference to the position of the reference mirror 12, the pivot point, a principal point of the eye E to be inspected. The scan angle θi' corresponds to a second angle between the eyeball axis of the eye E to be inspected and the actual measuring light scanning the inside of the eye E to be inspected. A light ray 80 in FIG. 6 is a light ray that scans the inside of the eye at the scan angle θi'. In order to calculate θi', it is necessary to suppose an optical mode of a human eye.

Figures 7, 8:
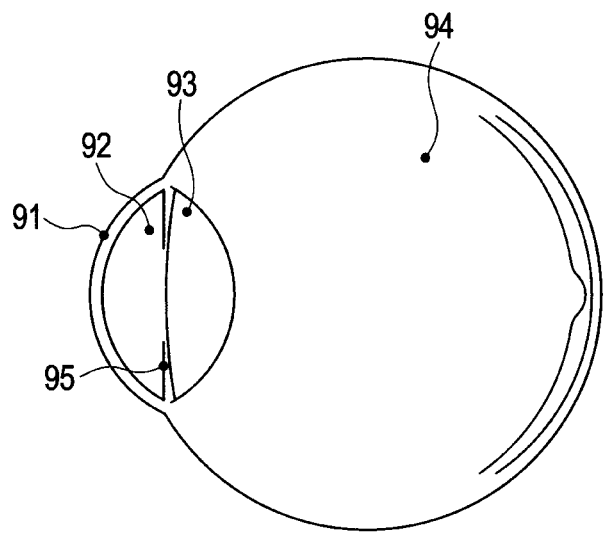
FIG. 7 is a diagram illustrating refracting elements of the eye to be inspected according to the first embodiment of the present invention.
FIG. 8 is a diagram illustrating a model of the refracting elements of the eye to be inspected according to the first embodiment of the present invention.

FIG. 7 illustrates modeled refracting elements of the eye to be inspected, which include a cornea 91, an anterior chamber 92, a crystalline lens 93, a corpus vitreum 94, and an iris surface 95. As to the curvature radius, thickness, and refractive index of each of the elements, a model indicated in the table of FIG. 8 is considered. Note that, the data about the optical information of the eye E to be inspected, such as the refractive indices of the refracting elements and the above-mentioned relationship between the incident angle θi and the scan angle θi', is stored in the memory 24 as a storage unit. Performing a calculation using those refracting elements, a front main surface of the eye is at a position of 1.6 mm from the cornea, and a rear main surface is at a position of 1.9 mm from the cornea. If the pivot point coincides with this main surface, Snell's law can be applied as follows.

$$\theta i' = a\sin\{(\sin\theta i)/Nvit\}$$

If the pivot point is different from the main surface, θi' can be determined more accurately by using a distance δpv between the pivot point and the rear main surface.

The focal length of the eye is denoted by feye, a distance between the cornea vertex and the front principal point is denoted by o1, a distance between the cornea vertex and a pivot imaging position (scan mirror conjugate position) is denoted by inpv, and the refractive index of the corpus vitreum is denoted by Nvit. Then, the following expression is satisfied.

$$\delta pv = (1/feye - 1/(o1-ipv))^{-1} \times Nvit$$

When the calculation is performed using the eye model illustrated in FIG. 8, feye is 17 mm and o1 is 1.8 mm. As described above, if the pivot point after the automatic alignment coincides with the iris surface 95, inpv is 3.5. If Nvit is 1.34, δpv becomes 1.8 mm.

In FIG. 6, a position 81 is a rear principal point position of the eye optical system. A position 82 is an apparent pivot position viewed from a retinal surface, and a distance from the rear principal point is δpv as described above. When a distance from the retinal surface of this pivot point is denoted by pv1, pv1=RmxL'−hj' is satisfied. A line segment 83 connecting a reach position of the measuring light on the CG surface and the principal point 81 of the eye E to be inspected and the light ray 80 passing through the iris surface 85 and the pivot point 82 cross on a surface 84 that passes an intersection of the optical axis (eyeball axis) and the retina and is perpendicular to the optical axis. Therefore, when a distance between the principal point 81 of the eye to be inspected and the pivot point 82 is denoted by δpv, the angle θi' can be expressed by the following expression.

$$\theta i' = a\tan((\delta pv + pv1) \times \tan(ref\theta i)/pv1)$$

Here, refθi=a sin(sin(θi)/Nvit) holds.

Using θi' determined in this way, an accurate shape of the retina can be expressed by the following expression using the polar coordinates (Step S905).

$$Image p(\theta i', RmxL'-hj')$$

(Image Data Indicating Actual Shape)

Using θi', hj', and RmxL' determined by the above-mentioned calculation, image data indicating an actual shape can be expressed by Image(x, y) in the orthogonal xy coordinates. Note that, the following expressions are satisfied.

$$x = (RmxL'-hj') \times \sin(\theta i')$$

$$y = RmxL' - \{(RmxL'-hj') \times \cos(\theta i')\}$$

The operator operates a display selection switch 20f and hence can selectively display a tomographic image close to an actual shape and an actual size calculated in this way (Step S907), or a normal tomographic image (based on the optical distance) (Step S908). In addition, a circle fitting to a pigment epithelium of the retina may be determined, and the curvature radius of the circle may be displayed as the curvature radius of the retina. Further, a partially fitting circle may be determined so as to display a distribution of the curvature radius thereof, or an approximate curve, such as a polynomial of each layer, may be determined so as to display the coefficients thereof. Note that the step of determining the image data expressing the actual shape as described above corresponds to a step of the present invention for correcting the tomographic image to be a tomographic image obtained corresponding to a second position on the optical path of the measuring light, which has an optical path length corresponding to the optical path length of the reference light different from the above-mentioned first position. This step is performed in the control portion 19 by a module region having a function as a tomographic image correction unit. Note that this second position is constituted of a value close to the above-mentioned actual size.

In other words, in the calculation of image data, the distance between the retina and the incident point (pivot point) of the measuring light entering the eye to be inspected may be determined based on the detected optical path length so as to perform the calculation using the optical path length. In addition, an angle between the eyeball axis and the measuring light at the incident point in the eye to be inspected may be determined so as to calculate the image data based on the angle. Note that the calculation described above is performed in the control portion 19 by a module region having a function as a calculation unit. The calculation unit calculates data about a second tomographic image based on the optical path length of the reference light and data about optical information of the eye to be inspected, which are obtained when the normal tomographic image is obtained from the eye to be inspected corresponding to a first tomographic image of the present invention, and a signal of the combined light corresponding to the normal tomographic image. In addition, the above-mentioned storage unit stores data about optical information of the eye to be inspected, which is used for performing the calculation by the calculation unit.

Figure 10:
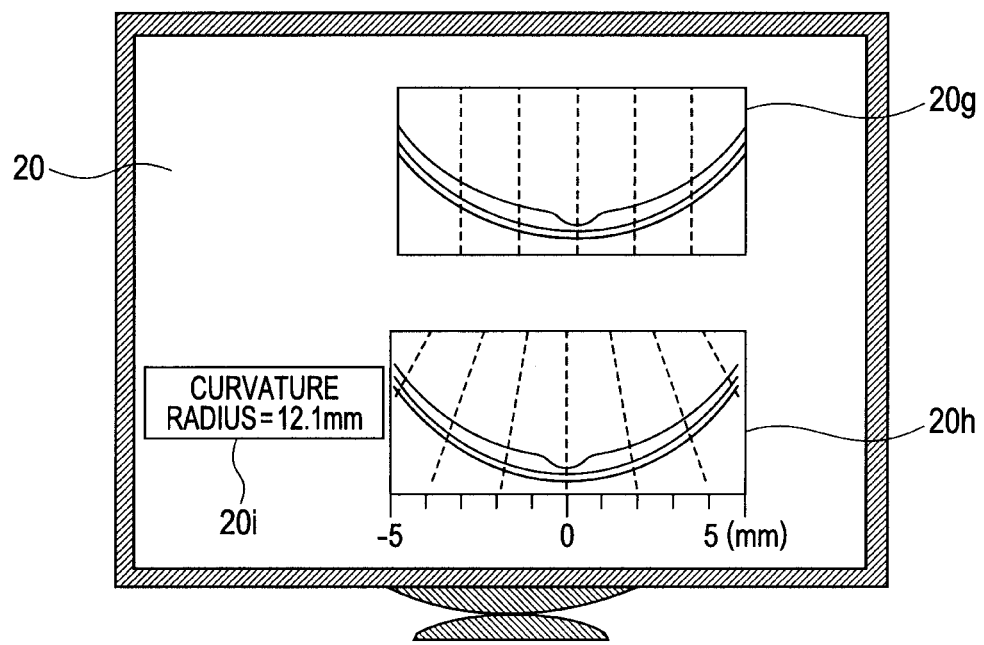
FIG. 10 is a diagram illustrating a display example of a tomographic image according to the first embodiment of the present invention.

FIG. 10 illustrates a display example of the tomographic image displayed on the display portion 20 as a display unit. FIG. 10 illustrates the tomographic image based on the optical distance displayed in a display region 20g and the tomographic image displayed in a display region 20h indicating an actual size and an actual shape determined according to this embodiment. Further, the display region 20h displays a scale indicating an actual size. This actual size can be determined from RmxL' and θi', and is displayed with reference to a position of the coherence gate at θ'=0. In addition, the curvature radius of the circle fitting to the retinal pigment epithelium is displayed in a display region 20i. Note that the two tomographic images may be displayed alternately based on a switching operation. The determination of the display form and the like on the display unit are performed in the control portion 19 by a module region having a function as a display control unit for determining the form.

In this way, according to this embodiment, a tomographic image that is close to an actual shape of the eye to be inspected can be obtained by determining the image data using optical information of the eye to be inspected (such as refractive indices of the refracting elements, and a relationship between the incident angle and the scan angle) and the optical path length. In addition, a tomographic image based on the optical distance and a tomographic image obtained according to this embodiment can be displayed in a comparison manner.

Note that this embodiment describes an example of a case where the refractive indices of the refracting elements and the relationship between the incident angle and the scan angle are stored in advance as optical information of the eye to be inspected. Note that the relationship between the incident angle and the scan angle described here corresponds to a relationship between a first angle between the measuring light entering the inside of the eye to be inspected and the optical axis of the eye to be inspected and a second angle as a scan angle formed between the measuring light inside the eye to be inspected and the optical axis of the eye to be inspected. However, the present invention is not limited to this mode, and it is possible to store at least one of those angles and to determine the other by the above-mentioned calculation or the like so as to reduce memory capacity. In addition, there may be adopted a mode in which an input unit to input the optical information directly is disposed, and the above-mentioned calculation unit performs the calculation based on the input value input by the input unit.

Second Embodiment (Three-Dimensional Shape)

The first embodiment describes the method of determining the image data of an actual size about the B-scan image in which one line of the fundus is scanned to display a tomographic image, but it is possible to scan the fundus surface in a two-dimensional manner so as to convert the three-dimensional image data for obtaining three-dimensional data into actual size data.

However, the OCT apparatus usually performs the two-dimensional scan by a tandem scan method in which X and Y scan mirrors are disposed to be close to each other. In the case of this method, the pivot point is different between the X scan and the Y scan. The positions of those pivot points may be determined from the design value. In addition, only the Y scan mirror is moved in a reciprocating manner by the same method as described above, a reflecting member is disposed at a position where the light ray image does not move (the pivot point Y of the scan mirror), and a reference mirror position Rmoy at which the position and the optical path length become the same is determined from the interfering signal so that the same calculation is performed. A result of the three-dimensional scan can be expressed as Image ($\theta xi$, $\theta yj$, hk), where $\theta xi$ denotes a scan angle of the X scan mirror, $\theta yj$ denotes a scan angle of the Y scan mirror, and hk denotes a distance from the coherence gate.

In the same manner as described above, using a reference mirror position Rmxl obtained when the image data is acquired, the image data in an actual size using the orthogonal x, y, and z axes can be expressed as follows.

$$x = (RmxL' - hk') \times \cos(\theta yj') \times \sin(\theta xi')$$

$$y = (RmyL' - hk') \times \cos(\theta xi') \times \sin(\theta yj')$$

$$z = RmxL' - (RmxL' - hk') \times \cos(\theta xi') \times \cos(\theta yj')$$

In this way, the reference mirror position is detected, and data of a fundus shape in an actual size can be generated based on the scan-mirror angle and light intensity data about the distance from the coherence gate (RmyL' is an actual distance in the eye to be inspected determined based on the optical distance RmyL from the pivot point by the Y scan mirror, similarly to RmxL'). Similarly to the above description, a fundus image in an actual size may be displayed based on this data, or the curvature radius of each portion may be calculated and displayed.

According to this embodiment, three-dimensional image data of the eye to be inspected can be further obtained.

Third Embodiment

In the first and second embodiments, optical elements of the eye are modeled to perform the calculation, and slightly different values of the constants are described in different documents. Therefore, the table as illustrated in FIG. 8 may be displayed on the monitor, and the user may be allowed to freely input the data values, such as the refractive indices of the refracting elements of the eye to be inspected, by using an input unit such as a mouse or a keyboard. In addition, the usability can be further improved by storing multiple constants in the memory 24 in advance and by allowing these values to be selected in a pull-down list or the like by a mouse operation of the person to be inspected. The usability can be further improved by including a constant of a non-crystal lens eye and a constant of an IOL eye to be inspected in the multiple constants.

In addition, it is possible to determine a more accurate shape, for example, by allowing for the input of data of the axial length, the refractive power, and the curvature radius of the cornea of the eye to be inspected, which are determined from measured values determined by an axial length measurement device, a refractometer, and a cornea shape measurement, respectively. The control portion determines the curvature radius and the thickness of the refracting element by calculation based on the input measured values, and calculates the angle $\theta'$ based on the data.

According to this embodiment, because the input value can be input and changed for each eye to be inspected, image data that is closer to the shape of the eye to be inspected can be obtained.

Other Embodiments

Further, the present invention is also implemented by executing the following processing. Specifically, in this processing, software (program) for implementing the functions of the above-mentioned embodiments is supplied to a system or an apparatus via a network or various kinds of storage medium, and a computer (or CPU, MPU, etc.) of the system or the apparatus reads and executes the program.

Note that in the embodiments described above, the case where an eye to be inspected is used as the object to be inspected and a retina is used as the region to be inspected is described as an example. However, the present invention is not limited thereto, and may be applied to various cases of photographing a tomographic image of a region to be inspected included in an object to be inspected that includes refracting elements thereinside.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-010150, filed Jan. 20, 2011, which is hereby incorporated by reference herein in its entirety.

What is claimed is:

1. An image photographing apparatus comprising:
   a detecting unit configured to detect combined light of return light from an eye and reference light, the return light being obtained by irradiating the eye with measuring light, the reference light corresponding to the measuring light;
   a scanning unit configured to scan the measuring light on the eye; and
   a unit configured to generate a tomographic image of a fundus of the eye in accordance with a calculation involving (1) data regarding an optical distance between a position optically conjugate with the scanning unit and a position in an optical path of the measuring light, corresponding to an optical path length of the reference light, (2) data, determined using a relationship between a first angle formed between the measuring light entering an inside of the eye to be inspected and an optical axis of the eye and a second angle formed between the measuring light inside the eye to be inspected and the optical axis of the eye, regarding the second angle, (3) the combined light detected by the detecting unit, and (4) data regarding a refractive index of a refractive element inside the eye.

2. An image photographing apparatus according to claim 1, further comprising a display control unit configured to cause a display unit to display the tomographic image generated by the generating unit.

3. An image photographing apparatus according to claim 1, wherein the image photographing apparatus further comprises a unit configured to input a value of the refractive index of the refracting element, and
   wherein the generating unit generates the tomographic image of the eye based on the value input by the unit for inputting.

4. An image photographing apparatus according to claim 1, further comprising:
   an adjustment unit configured to adjust the optical path length by moving along an optical axis of the reference light; and
   a detection unit configured to detect the optical path length based on a movement distance of the adjustment unit.

5. An image photographing apparatus according to claim 1, further comprising a unit configured to acquire a first tomographic image of a fundus of the eye, based on the detected combined light, and
   wherein the generating unit corrects the first tomographic image to generate a second tomographic image in accordance with the data regarding the optical distance, the data regarding the second angle, and the data regarding the refractive index, so as to generate the tomographic image of the fundus of the eye.

6. An image photographing method comprising the steps of:
   detecting combined light of return light from an eye and reference light, the return light being obtained by irradiating the object with measuring light, the reference light corresponding to the measuring light;
   scanning the measuring light on the eye by a scanning unit; and
   generating a tomographic image of a fundus of the eye in accordance with a calculation involving (1) data regarding an optical distance between a position optically conjugate with the scanning unit and a position in an optical path of the measuring light, corresponding to an optical path length of the reference light, (2) data, determined using a relationship between a first angle formed between the measuring light entering an inside of the eye to be inspected and an optical axis of the eye and a second angle formed between the measuring light inside the eye to be inspected and the optical axis of the eye, regarding the second angle, (3) the detected combined light, and (4) data regarding a refractive index of a refractive element inside the eye.

7. A non-transitory tangible medium having recorded thereon a program for causing a computer to perform steps of the image photographing method according to claim 6.

8. An image photographing method according to claim 6, further comprising a step of acquiring a first tomographic image of a fundus of the eye, based on the detected combined light, and
   wherein in the step of generating the tomographic image, the first tomographic image is corrected to generate a second tomographic image in accordance with the data regarding the optical distance, the data regarding the second angle, and the data regarding the refractive index, so as to generate the tomographic image of the fundus of the eye.

9. An image photographing method according to claim 6, further comprising a step of calculating a shape of the fundus of the eye in the generated tomographic image.

10. An image photographing apparatus according to claim 1, further comprising a calculation unit configured to calculate a shape of the fundus of the eye in the generated tomographic image.

11. An image photographing apparatus according to claim 1, wherein the position optically conjugate with the scanning unit is a pivot point, and the position in the optical path of the measuring light, corresponding to the optical path length of the reference light is a coherence gate.

12. An image photographing apparatus according to claim 1, wherein the refractive index is a refractive index of a corpus vitreum of the eye.

13. An image photographing apparatus according to claim 1, wherein the unit generates the tomographic image in accordance with (1) the data regarding the optical distance, (2) the data regarding the second angle, (3) the combined light, (4) the data regarding the refractive index of the eye, and (5) an optical distance between (a) the position in the optical path of the measuring light, corresponding to the optical path length of the reference light, and (b) layer of a retina of the eye.

* * * * *